US008980365B2

(12) United States Patent
Biemans

(10) Patent No.: US 8,980,365 B2
(45) Date of Patent: Mar. 17, 2015

(54) METHOD OF PROTECTING BIOLOGICALLY ACTIVE SUBSTANCES AGAINST DENATURATION

(76) Inventor: Rogier Biemans, Nijmegen (NL)

(*) Notice: Subject to any disclaimer, the term of this patent is extended or adjusted under 35 U.S.C. 154(b) by 0 days.

(21) Appl. No.: 14/000,588

(22) PCT Filed: Feb. 29, 2012

(86) PCT No.: PCT/EP2012/053454

§ 371 (c)(1),
(2), (4) Date: Aug. 20, 2013

(87) PCT Pub. No.: WO2012/119907

PCT Pub. Date: Sep. 13, 2012

(65) Prior Publication Data

US 2013/0337150 A1 Dec. 19, 2013

(30) Foreign Application Priority Data

Mar. 9, 2011 (EP) .................................... 11157399

(51) Int. Cl.

| | |
|---|---|
| ***A61L 33/00*** | (2006.01) |
| ***A61F 13/00*** | (2006.01) |
| ***B05D 1/02*** | (2006.01) |
| ***A61M 5/00*** | (2006.01) |
| ***A61M 5/158*** | (2006.01) |
| ***A61L 26/00*** | (2006.01) |
| ***A61K 9/00*** | (2006.01) |
| ***A61K 9/16*** | (2006.01) |
| ***A61K 9/70*** | (2006.01) |
| ***B41J 2/14*** | (2006.01) |
| *A61M 37/00* | (2006.01) |

(52) U.S. Cl.
CPC ........... *A61L 26/0061* (2013.01); *A61K 9/0021* (2013.01); *A61K 9/1623* (2013.01); *A61K 9/7007* (2013.01); *B41J 2/14274* (2013.01); *A61K 9/1652* (2013.01); *A61M 37/00* (2013.01)
USPC ......... 427/2.31; 427/2.1; 427/421.1; 604/173

(58) Field of Classification Search
USPC ............................... 427/2.31, 421.1; 604/173
See application file for complete search history.

(56) References Cited

U.S. PATENT DOCUMENTS

| | | | | |
|---|---|---|---|---|
| 7,153,472 | B1 * | 12/2006 | Bronshtein | 422/41 |
| 7,354,597 | B2 | 4/2008 | Johnson et al. | |
| 2004/0115167 | A1 * | 6/2004 | Cormier et al. | 424/85.1 |
| 2007/0248571 | A1 * | 10/2007 | Masada et al. | 424/85.4 |
| 2008/0026040 | A1 | 1/2008 | Farr et al. | |
| 2010/0280457 | A1 * | 11/2010 | Tokumoto et al. | 604/173 |

FOREIGN PATENT DOCUMENTS

| | | | |
|---|---|---|---|
| JP | 2003154655 | A * | 5/2003 |
| WO | 2007/018887 | A2 | 2/2007 |

* cited by examiner

*Primary Examiner* — Cachet Sellman
(74) *Attorney, Agent, or Firm* — Richard M. Goldberg

(57) ABSTRACT

A method of protecting a biologically active substance against denaturation, wherein a liquid (14) containing the active substance and a matrix-forming substance are deposited on a target surface (18) and dried so as to form a solid amorphous matrix (26) with the molecules of the active substance embedded therein, wherein an ink jet printer (10) is used for depositing the liquid (14) on the target surface (16) in the form of droplets (12) having a volume small enough to cause the liquid to dry when it impinges on the target surface (16) and to be held on the target surface through adhesion.

11 Claims, 3 Drawing Sheets

METHOD OF PROTECTING BIOLOGICALLY ACTIVE SUBSTANCES AGAINST DENATURATION

BACKGROUND OF THE INVENTION

The invention relates to a method of protecting a biologically active substance against denaturation, wherein a liquid containing the active substance and a matrix-forming substance are deposited on a target surface and dried so as to form a solid amorphous matrix with the active substance embedded therein.

Numerous active pharmaceutical ingredient molecules and protein molecules for therapeutic or prophylactic treatment or diagnosis are known to be susceptible to denatuation, e.g. to breakdown or irreversible deformation.

In order to be able to keep the active substances stable during storage at ambient temperature, it has been known to suspend the active molecules in a stabilizing substance which is then transformed into an amorphous solid (glassy) state either by freeze drying or spray drying.

However, freeze drying has the drawback that it requires expensive equipment and long processing times. Further, the active molecules may be damaged by the formation of ice crystals in the freezing process. Frequently, a cumbersome post processing of the freeze-dried product is necessary in order to bring it into a state ready for administration.

On the other hand, spray drying has the disadvantage that a considerable portion of the product remains in the spray dryer, so that the yield of the dried active substance is low. Further, the active molecules may be damaged as a result of exposure to high temperatures during the drying process. Frequently, an additional drying step is necessary in order to reduce the residual moisture.

U.S. Pat. No. 7,354,597 discloses a method wherein microquantities (between 1 nl and 10 pl) of a liquid with the stabilizing substance and the active substance suspended therein are deposited in microscale reservoirs, i.e. concave-shaped structures on a target surface, and are then dried with or without a freezing step. Injection and ink jet printing are mentioned as examples of suitable deposition methods.

SUMMARY OF THE INVENTION

It is an object of the invention to provide a method of the type indicated above, which can be implemented at low costs and with high efficiency and results in products that facilitate the administration of the active substance.

According to the invention, this object is achieved by using an ink jet printer for depositing the liquid on the target surface in the form of droplets having a volume small enough to cause the liquid to dry when it impinges on the target surface and to be held on the target surface through adhesion.

Thus, the substance containing the active substance is simply "printed" onto a substrate which does not have to form microcavities but may have a flat or even convex surface because the liquid droplets, thanks to their small volume, will dry immediately when they impinge on the surface and will then stick to that surface through natural adhesion.

The low volume of the droplets has the further effect that most of the volatile components will evaporate immediately when the droplet hits the target surface, so that the substance printed onto the substrate will have a very low residual moisture and the post-drying step is simplified and may be performed in an inline process right after printing, for example, or no post-drying is needed at all.

More specific optional features of the invention are indicated in the dependent claims.

The rapid drying of the small liquid volume results in the formation of a glassy solid without requiring a large temperature change rate. Consequently, the entire process may be performed at moderate temperatures, e.g. at ambient temperature, and will nevertheless reliably result in an amorphous solid which is suitable for stabilizing the active molecules. More specifically, the volume of droplets should be so small that, when the substrate with the liquid jetted thereon is left at room temperature for four minutes or less and one then wipes with a finger over the deposited material, it does not feel sticky and cannot be wiped off.

The substrate that forms the target surface may be made of any suitable material and may have any suitable shape and may conveniently be configured already for the later administration of the active substance. For example, the substrate may be a patch that is applied to the skin of a patient so as to release the active molecules through the skin. If the patch, e.g., a polycarbonate patch, is equipped with transcutaneous needles to penetrate the skin, the active substance may also be printed directly onto the surface of the needles. In other embodiments, the substrate may be a transcutaneous needle, a drug dispensing implant or a porous membrane through which a liquid is pressed in order to administer the active substance. The membrane may be used for treating an infusion liquid or may also form part of a drug dispensing implant. Of course, it is also possible that the active substance is just printed on any surface from which it will later be washed off in order to dissolve the active substance in a liquid.

The equipment that is needed for practicing the invention consists essentially of a low-cost commercial ink jet printer. A piezoelectric ink jet printer is preferred, but a thermal (bubble jet) ink jet printer may also be used.

The "biologically active substance" which may be stabilized with the method according to this invention may be any substance that after administration to an animal or human interferes with its normal metabolism (other then regular digestion), in particular substances that are either biopolymers such as proteins or polysaccharides or live or killed micro organisms such as bacteria, viruses and rickettsia, or derivates of these live or killed micro organisms. In particular, the biologically active substances are antigens for use in a vaccine, i.e. a constitution for preventing, mitigating or curing an infection with a pathogenic micro organism. Other examples are proteins and protein sub-units, cytokines, other immune-regulating molecules, saponines and the like. Adjuvants such as alu-gels may also be added.

The liquid to be deposited with the ink jet printer is preferably an aqueous liquid, although other solvents may be used, especially for non-proteins. The matrix-forming substance may be any commonly used lyophilisation formulation and should preferably contain a (small) molecule that can provide H-bonds with the proteins of the active substance. For example, mono-, di- or oligosaccharides or amino acids may be used. Preferably, a polymer such as dextran, gelatine, BSA and the like may be added in order to increase the glass transition temperature Tg. Preferably, the glass transition temperature of the solid formed on the target surface is in the range from 20 to 60° C. In certain applications, it may however be as high as 150 or 170° C.

A surfactant may be added to improve the performance of the liquid in the ink jet printer and/or the deposition or coating characteristics.

BRIEF DESCRIPTION OF THE DRAWINGS

Preferred embodiments will now be described in conjunction with the drawings, wherein.

DETAILED DESCRIPTION

Figure 1:
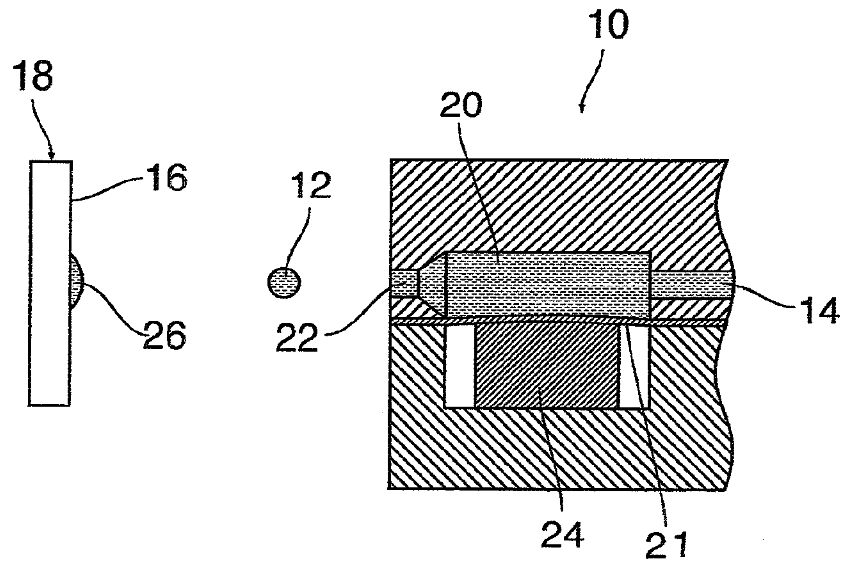
FIG. 1 is a schematic cross-sectional view of a system for practicing the invention.

As is shown in FIG. 1, an ink jet printer 10 is used for jetting droplets 12 of a liquid 14 onto a target surface 16 of a substrate 18. The liquid 14 may be a water-based liquid containing a sugar such as sucrose as matrix-forming substrate, a polymer, and a surfactant. An active substance which is to be protected against denaturation is suspended or dissolved in the liquid.

In the inkjet printer 10, the liquid is supplied to a chamber 20 that opens out into a nozzle 22. A piezoelectric actuator 24 is rigidly supported in the printer and is separated from the chamber 20 by a flexible sheet 21. When a voltage is applied to the actuator 24, the latter is deformed abruptly, so that the sheet 21, is deflected into the chamber 20, thereby generating an acoustic pressure wave in the liquid 14. The pressure wave propagates towards the nozzle 22 and causes the droplet 12 to be ejected from the nozzle. The volume of the droplet 12 is smaller than 500 pi, preferably smaller than 100 pi or 10 pi and even more preferably in the range of 2 to 5 pi.

When the droplet 12 hits the target surface 16, it spreads on this surface, and since the volume of the droplet is small, the surface/volume ratio becomes so large that the energy of the droplet is sufficient for evaporating almost all of the water contained therein. The non-volatile components (formed mainly by the sugar) form a solid amorphous matrix 26 which sticks to the substrate 18 by natural adhesion and in which the molecules of the active substance are embedded. OH-groups of the sugar replace the OH in the water and form H-bonds with the molecules of the active substance, so that these molecules are stabilized and protected against degradation.

It will be understood that the print process that has been described above can be performed at ambient temperature, e.g. at a temperature between 2 and 30° C., although higher temperatures may be used, depending on the nature of the active substance. In general, a heating or cooling of the liquid 14 is not necessary, so that the energy consumption is reduced significantly in comparison to freeze drying or spray drying.

It will further be understood that the ink jet printer 10 may comprise a plurality of nozzle and actuator units arranged in one or more rows, and these units may fire at a high frequency, so that the matrix 26 on the substrate 18 forms a continuous layer when the printhead of the printer 10 is moved across the target surface. As in conventional ink jet printing, the printer may also be controlled to form any desired pattern on the matrix.

Figure 2:
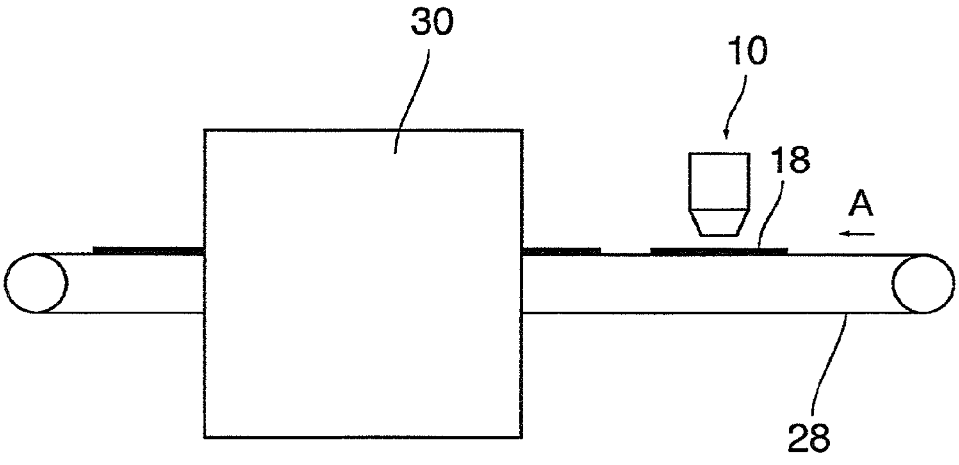
FIG. 2 is a schematic view of a production line employing the method according to the invention.

FIG. 2 shows an example of a production line wherein the substrates 18, e. g. medical patches, are successively placed onto a conveyer belt 28 on which the substrates are moved past the ink jet printer 10 in the direction of an arrow A. The ink jet printer prints a continuous layer or any suitable pattern of amorphous material containing the active substance onto the target surface 16 of the substrates. Then, the conveyer belt 28 feeds the substrates through an oven 30 wherein the substrates are heated to a moderate temperature to remove residual moisture from the amorphous material without degrading the active substance. Then, the substrates 18 may be taken off the conveyer belt and may immediately be packaged and shipped or stored.

Figure 3:
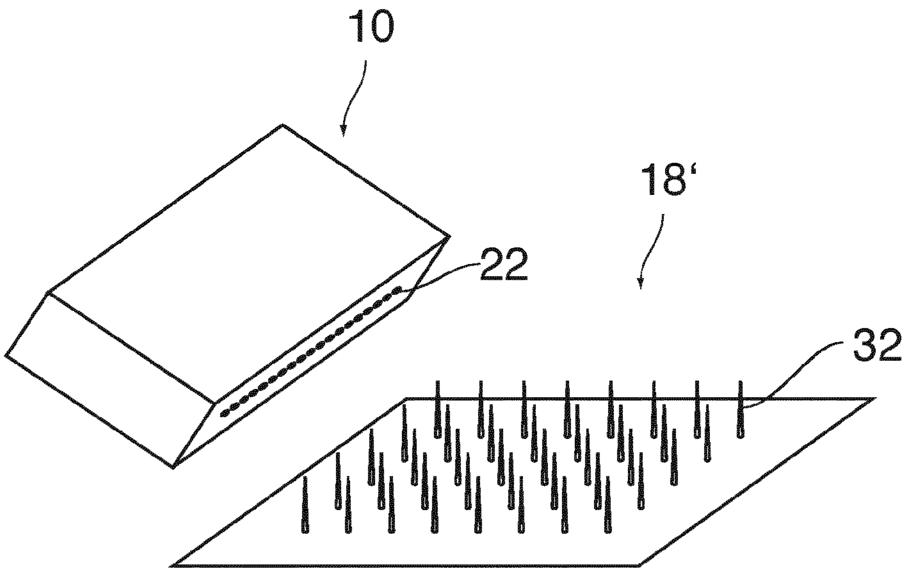
FIG. 3 is a perspective view of an ink jet printer and a substrate used in the present invention.

FIG. 3 illustrates a substrate 18' which takes the form of a polycarbonate patch which has a plurality of subcutaneous (micro-) needles 32 which penetrate the skin of a patient when the patch is applied. In this example, the ink jet printer 10 is arranged obliquely relative to the substrate 18' so that, when the substrate passes below the printer, the droplets may be ejected onto both, the surface of the patch and the surfaces of the needles 32.

Figure 5:
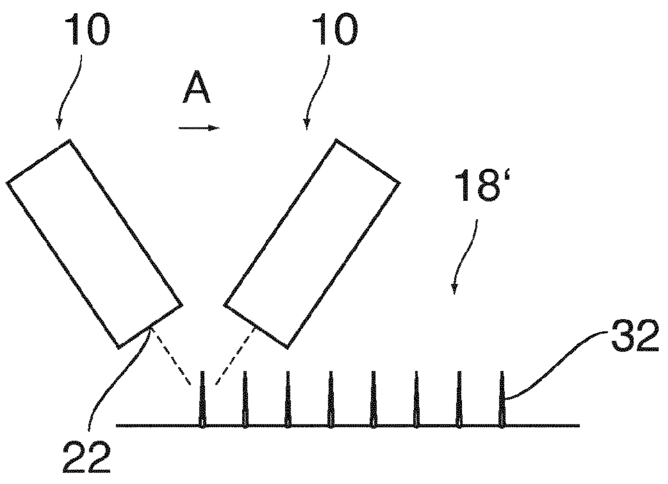
FIGS. 5(A) and (B) are a side view and a top plan view, respectively, of a modified printer arrangement for printing onto the substrate shown in FIG. 3.
Figure 5:
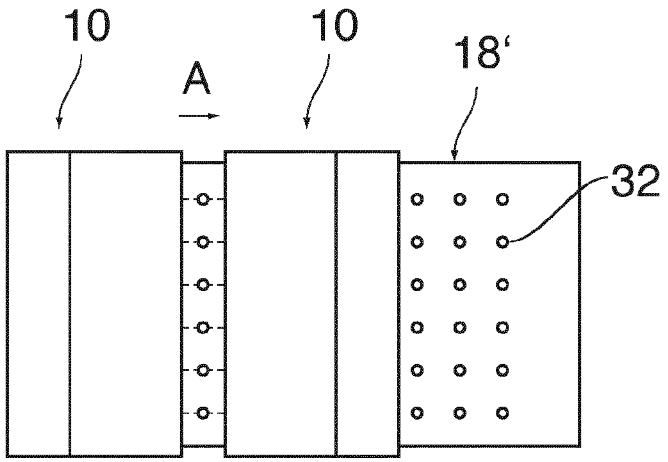

In a preferred embodiment, shown in FIGS. 5(A) and (B), the nozzles 22 of two printers 10 are aligned with the rows of needles 32 and the printers are jointly moved across the substrate 18' in the direction of arrow A and are controlled such that the droplets are targeted onto the needles only. Optionally, two or more printers may be used for obliquely jetting the droplets onto the needles from different sides, and/or the substrate may be scanned in several passes with varying heights of the printer(s) relative to the needles, so that almost the entire peripheral surface of the needles may be coated and/or the dose of the active substance may be controlled by controlling the length of the needle portion that is being coated.

Figure 6:
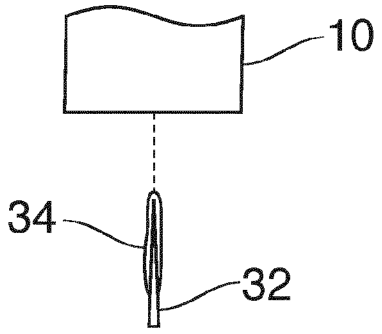
FIG. 6 is a side view of yet another printer and substrate arrangement.

As an alternative, shown in FIG. 6, a single printer 10 may be arranged with its jetting direction normal to the plane of the substrate 18', i.e. in parallel with the needles, and controlled such that the droplets will hit the tips of the needles 32 so as to form a coating 34 thereon.

Figure 4:
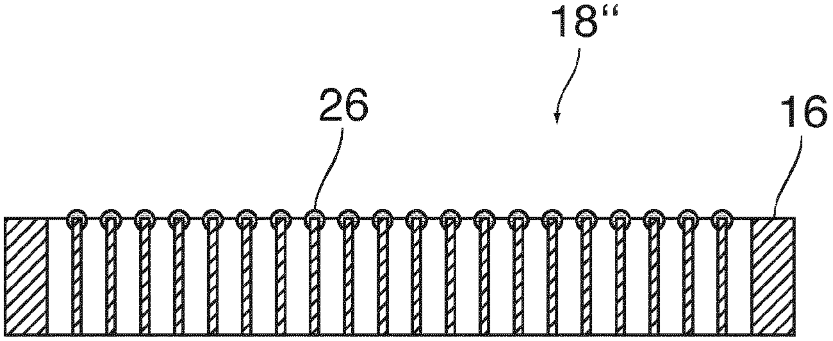
FIG. 4 is a cross-sectional view of a product obtained by the method according to the invention.

As a result, the active substance can be administered to the patient with high efficiency. In another embodiment, shown in FIG. 4, the substrate may take the form of a porous membrane 18" with the matrix 26 printed on the top target surface 16 thereof. When a liquid, e.g. an infusion liquid, is pressed through the pores of the membrane from below, the bulk material will be dissolved and the active substance will be released into the liquid. When the membrane 18" has a regular pattern of pores, the printer may be controlled to print only on the edges of the pores.

More specific embodiments will be described in the examples below.

EXAMPLE 1

A liquid containing 40% w/t sucrose, and 1% polysorbate 80 in water was printed on a substrate made of transparent nitrocellulose with a piezo-type ink jet printer. A solid coating was formed which firmly adhered to the substrate and was difficult to wipe off. The glass transition temperature Tg of the coating was determined in a DSC test and was found to be 35° C.

EXAMPLE 2

A liquid containing 20% w/t sucrose, 5% dextran 70 and 2% polysorbate 80 was printed under the same conditions as in example 1. The resulting coating on the substrate was difficult to wipe off and had a Tg of 47° C.

The invention claimed is:

1. A method of protecting an active substance against denaturation, comprising the steps of:

depositing a liquid containing the active substance and a matrix-forming substance on a convex target surface of which at least a part of the target surface is formed by a surface of subcutaneous needles, by at least one ink jet printer in the form of droplets having a volume small enough to cause the liquid to dry when it impinges on the target surface and to be held on the target surface through adhesion, said step of depositing including the steps of:

moving at least one said ink jet printer across a regular array of the subcutaneous needles, controlling said at least one said ink jet printer to print onto the needles only, and directing nozzles of said at least one said ink jet printer onto tips of the needles with a jetting direction parallel with a direction of extension of the needles; and drying said deposited liquid so as to form a solid amorphous matrix with molecules of the active substance embedded therein.

2. The method according to claim 1, wherein the volume of the droplets is less than 500 pl.

3. The method according to claim 1, wherein the target surface is formed on a medical patch which has the subcutaneous needles.

4. The method according to claim 1, wherein the at least one ink jet printer is a piezoelectric ink jet printer.

5. The method according to claim 1, wherein the matrix-forming substance includes a saccharide.

6. The method according to claim 1, wherein the liquid includes a polymer in an amount to adjust a glass transition temperature Tg of the amorphous matrix to a value between 20 and 200° C.

7. The method according to claim 1, wherein the liquid includes a surfactant.

8. The method according to claim 1, wherein the liquid, when it is jetted onto the target surface, has a temperature between 4 and 60° C.

9. The method according to claim 2, wherein the volume of the droplets is less than 100 pl.

10. The method according to claim 8, wherein the liquid, when it is jetted onto the target surface, has a temperature between 4 and 50° C.

11. The method according to claim 9, wherein the liquid, when it is jetted onto the target surface, has a temperature between 4 and 45° C.

* * * * *